(12) United States Patent
Grewe et al.

(10) Patent No.: US 9,364,636 B2
(45) Date of Patent: Jun. 14, 2016

(54) STEERABLE INTRALUMINAL MEDICAL DEVICE

(71) Applicant: Cook Medical Technologies LLC, Bloomington, IN (US)

(72) Inventors: David Douglas Grewe, West Lafayette, IN (US); Kevin Matthew Blum, Lanesville, IN (US); Richard Dean Hadley, Otterbein, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 51 days.

(21) Appl. No.: 14/528,853

(22) Filed: Oct. 30, 2014

(65) Prior Publication Data

US 2015/0119801 A1 Apr. 30, 2015

Related U.S. Application Data

(60) Provisional application No. 61/898,315, filed on Oct. 31, 2013.

(51) Int. Cl.
*A61M 25/01* (2006.01)
*A61M 25/09* (2006.01)

(52) U.S. Cl.
CPC ....... *A61M 25/0147* (2013.01); *A61M 25/0136* (2013.01); *A61M 2025/09116* (2013.01)

(58) Field of Classification Search
CPC ..................... A61M 25/0147; A61M 25/0136; A61M 2025/09116; A61B 2017/32002; A61B 2017/0003; A61B 2017/00314; A61B 2017/00318; A61B 1/0052
See application file for complete search history.

(56) References Cited

U.S. PATENT DOCUMENTS

| | | | |
|---|---|---|---|
| 4,503,842 A * | 3/1985 | Takayama | A61B 1/0052 200/6 A |
| 4,838,859 A | 6/1989 | Strassmann | |
| 5,190,050 A | 3/1993 | Nitzsche | |
| 5,195,968 A | 3/1993 | Lundquist et al. | |
| 5,273,535 A | 12/1993 | Edwards et al. | |
| 5,315,996 A | 5/1994 | Lundquist | |
| 5,549,542 A * | 8/1996 | Kovalcheck | A61B 1/0052 600/146 |
| 5,666,970 A | 9/1997 | Smith | |
| 5,667,476 A * | 9/1997 | Frassica | A61B 1/0052 600/139 |
| 6,648,875 B2 | 11/2003 | Simpson et al. | |
| 7,493,156 B2 | 2/2009 | Manning et al. | |
| 8,137,308 B2 | 3/2012 | Schultz | |
| 8,465,442 B2 | 6/2013 | Freed | |

FOREIGN PATENT DOCUMENTS

EP 0199870 B1 11/1986

\* cited by examiner

*Primary Examiner* — Quynh-Nhu H Vu
(74) *Attorney, Agent, or Firm* — Brinks, Gilson & Lione

(57) ABSTRACT

A steerable intraluminal medical device is described for use in navigating small diameter and curving arteries. The device includes a control handle that adjusts the direction of deflection of the tip throughout a 360° range of motion around the axis on the distal end. An optional locking mechanism is provided to maintain the desired angle of deflection during an intravascular procedure.

20 Claims, 4 Drawing Sheets

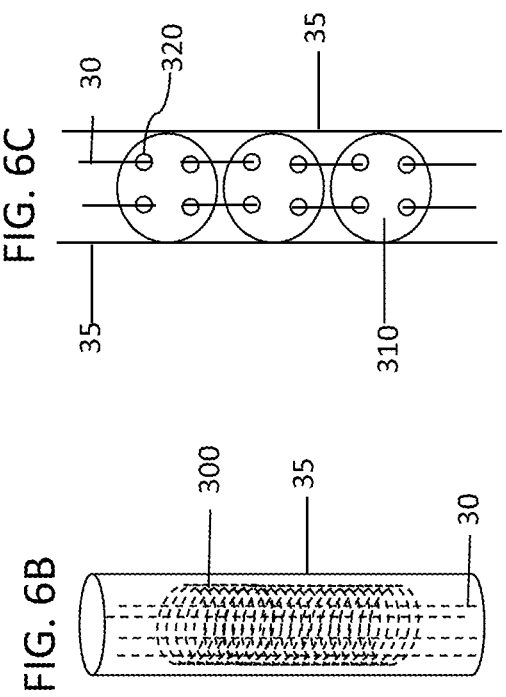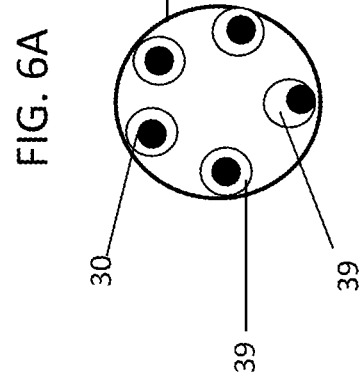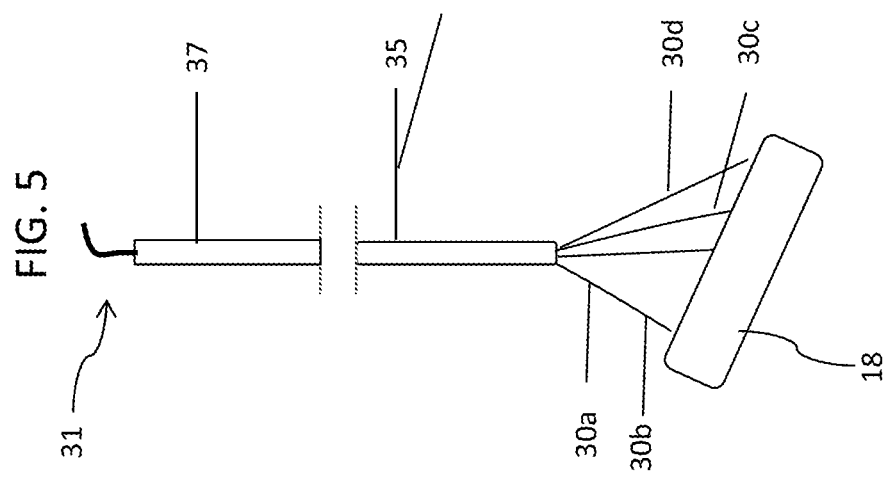

STEERABLE INTRALUMINAL MEDICAL DEVICE

RELATED APPLICATIONS

The present patent document claims the benefit of the filing date under 35 U.S.C. §119(e) of Provisional U.S. Patent Application Ser. No. 61/898,315, filed Oct. 31, 2013, which is hereby incorporated by reference.

TECHNICAL FIELD

The present invention relates to a steerable intraluminal medical device for navigating small diameter arteries.

BACKGROUND

Small diameter and curving arteries, such as the internal carotid artery, the posterior, middle or anterior cranial arteries, or the Circle of Willis are challenging pathways through which to advance a guidewire or catheter. When a wire guide—especially a small diameter, highly flexibly-tipped wire guide—encounters a right angle bend in an artery, advancing it further usually leads to its bowing outward from the bend and not advancing through the artery. Also, cerebral arteries are very tortuous and have thinner and weaker walls than other arteries. Thus, cerebral arteries present the risk of possible arterial wall perforation during vascular intervention.

Previously, guidewire tip curvature could be formed and changed only by removing the guidewire and reshaping it by hand. This increases the cost and complexity associated with an interventional procedure. Thus, there exists a need for a guidewire that can be steered through tortuous and small arteries without the need to remove the guidewire and reshape its tip.

SUMMARY OF THE INVENTION

This invention provides a steerable intraluminal medical device, such as a guidewire, for use in interventional vascular procedures, such as in the treatment of aneurysms or to remove embolic material. The guidewire of the invention is steerable and capable of navigating narrow and tortuous arteries such as in the cerebral vasculature. The tip of the guidewire may deflect throughout a 360° range about the axis of the guidewire. The guidewire's small diameter, flexibility and controlled omnidirectional tip avoids the problems associated with existing guidewires.

The tip of the guidewire can change curvature to facilitate entering a tortuous arterial lumen. When it is deflected, the tip is stiffer than when straight. This enhances its ability to traverse the curve. After the curve is traversed, the tip curvature may then be externally adjusted to match the geometry of the next pathway through which it must pass. If at any time it is desired to maintain a particular tip shape, the handle of the invention may be locked in order to do so. This is intended to help maintain its location in the artery.

The invention includes a handle portion that controls the angle of deflection of the tip of the guidewire. The handle includes a housing and within the housing is the operative mechanism for controlling the angle of deflection of the tip of the guidewire. The handle controls the angle of deflection of the tip by selectively adjusting the tension in the wires that make up the guidewire. Tension in the wires is adjusted by orienting a cable attachment disc according to the desired angle of deflection of the tip of the guidewire. The orientation of the cable attachment disc is controlled by use of a control button to move a series of wheels and rods on the interior of the handle that are operatively connected to the wire attachment disc.

In one aspect, the invention provides an intraluminal medical device including a handle, a plurality of wires, and a sheath that surrounds a portion of the plurality of wires. The handle includes a housing that has an interior and an exterior. Inside the handle is a first wheel that is rotatably mounted on the interior of the housing. A control button is disposed on the housing and has a top surface that is actuatable by an operator. A first force-transmittal rod, having a first end and a second end, is connected to the control button at the second end and connected to the first wheel at the first end. The connection between the first force-transmittal rod and the first wheel allows rotation of the first wheel. A wire attachment disc is also disposed on the housing and connected to the first wheel by a first force-receiving rod. The first force-receiving rod has a first end and a second end, the second end being connected to the wire attachment disc and the first end being connected to the first wheel. The connection between the first force-receiving rod and the first wheel allows rotation of the first wheel. Attached to the handle is a plurality of wires, where the wires of the plurality of wires have proximal ends and distal ends, the proximal ends being attached to the handle at the wire attachment disc. The plurality of wires are operatively joined at their distal ends. A sheath surrounds a portion or substantially all of the plurality of wires.

In certain embodiments, the handle includes second and third wheels, second and third force-transmittal rods, and second and third force-receiving rods.

In another aspect of the invention, the handle includes a first wheel, a second wheel, and a third wheel, each of which is rotatably mounted on the interior of a housing. A control button is operatively connected to the first, second and third wheels such that movement of the control button independently controls rotation of the first, second, and third wheels. In certain embodiments, a forward movement of the control button rotates the first and second wheels in a first direction and the third wheel in a second direction opposite the first direction; and a side-to-side movement of the control button rotates the first and second wheels in opposite directions. In this aspect, the first, second, and third wheels are also operatively connected to a wire attachment disc such that independent rotational movement of the first, second, and third wheels changes the orientation of the face of the wire attachment disc. In certain embodiments, rotation of the first and second wheels in the first direction tilts the wire attachment disc away from a vertical orientation and rotation of the first and second wheels in opposite directions twists the wire attachment disc around its vertical axis. A plurality of wires having proximal ends and distal ends are attached to the handle at the wire attachment disc at the proximal ends of the wires. A portion of the plurality of wires is surrounded by a sheath, which has proximal and distal ends.

In certain embodiments of the invention, a pivot plate is provided in the interior of the housing, where a pivot rod spaces the control button from the pivot plate.

In certain embodiments, the handle also includes an optional locking mechanism to lock the tip of the guidewire in a desired configuration. The locking mechanism, for example, can have a set of locking arms that engage the first, second, and third wheels to prevent their rotational motion. The set of locking arms can be controlled by a locking button that is accessible through a third opening located in the bottom of the housing.

BRIEF DESCRIPTION OF THE DRAWINGS

FIG. 5 illustrates the deflection of the tip of the guidewire at the distal end by changing the orientation of the face of the wire attachment disc.

FIG. 6A illustrates a cross-sectional view of an embodiment of the sheath having channels extending therethrough.

FIG. 6B illustrates an exemplary configuration where the wires extend through an internal spring within the sheath.

FIG. 6C illustrates another exemplary embodiment where the wires pass through a series of articulated spheres.

DETAILED DESCRIPTION

Figure 1A:
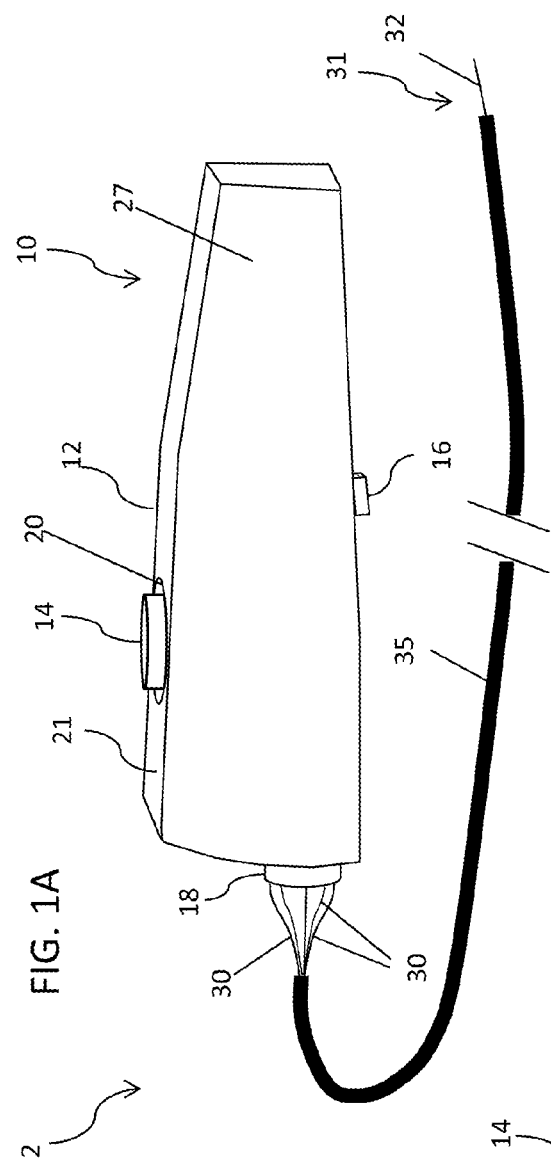
FIG. 1A shows a side perspective view of an embodiment of a steerable guidewire and handle.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly. For example, although the description below generally refers to a steerable guidewire assembly, the invention includes any type of steerable intraluminal medical device, including catheters.

Figure 1C:
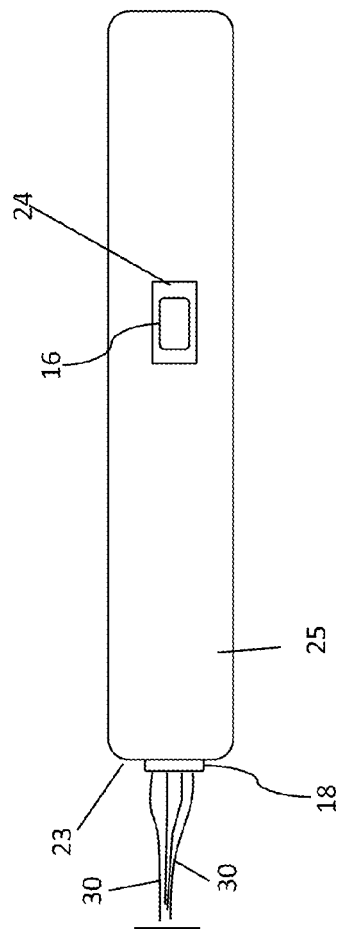
FIG. 1C shows a bottom view of an exemplary embodiment of the handle of the steerable guidewire.
Figure 1B:
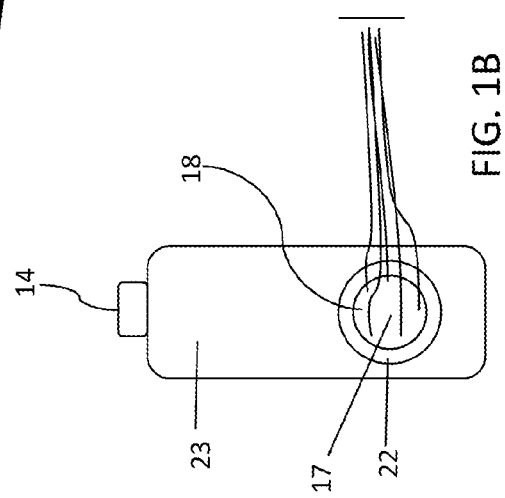
FIG. 1B shows a front view of an exemplary embodiment of the handle of the steerable guidewire.

Illustrated in FIGS. 1A-1C is an exemplary embodiment of a steerable guidewire assembly 2 of the invention. A handle 10 is attached to a plurality of wires 30 at the wire attachment disc 18. Wires 30 may be enclosed in a sheath 35 and a portion 32 of the plurality of wires 30 may extend beyond the sheath 35 at the distal end 31 of the plurality of wires 30. The portion 32 of the plurality of wires 30 may be surrounded by a flexible spring or coil, as described herein below, but which is not shown in FIG. 1A for clarity. The proportion of the wire extending beyond the sheath is for illustration purposes only and does not necessarily represent the actual dimensions.

Figure 4:
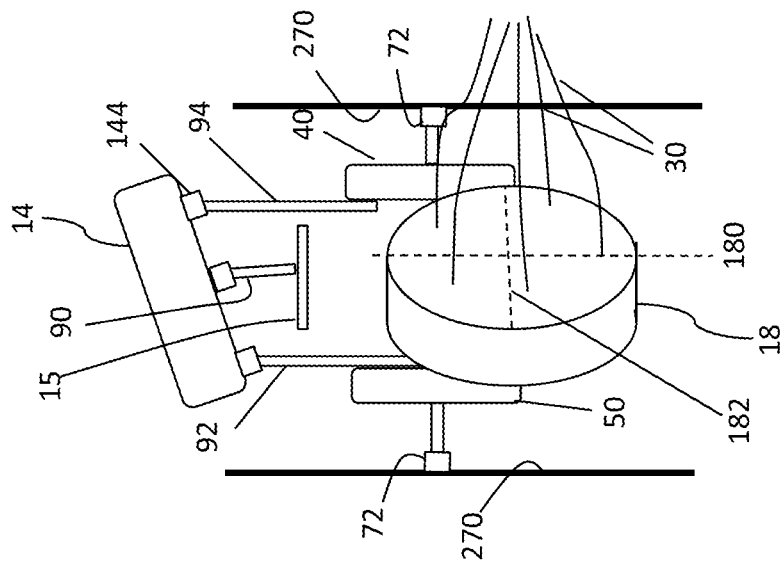
FIG. 4 illustrates a representative configuration viewed from the front where the face of the wire attachment disc is twisted to the left about its vertical axis by movement of the control button to the side.

The handle portion 10 may include a housing 12 that surrounds the working mechanism for controlling the orientation of the distal end of the plurality of wires 30. The housing 12 has an interior, an exterior, a top 21, a front 23, a bottom 25 and two sides 27 that comprise side inner walls 270 (FIG. 4). In the exemplary embodiment of FIGS. 1A-1C, the housing 12 also has a first opening 20, through which projects a control button 14 used to control the orientation of the wire attachment disc 18 and the distal end 31. The wire attachment disc 18 occupies a second opening 22 in the housing 12. An optional locking button 16 is situated on the bottom 25 of the handle 10 projecting through a third opening 24 in the housing 12. The handle 10 is preferably of a size and shape that allow an operator to comfortably and conveniently grasp the handle in one hand while permitting the manipulation of the control button 14 and locking button 16 with the thumb and fingers. Although the control button 14 in FIGS. 1A through 4 is shown as having a substantially flat upper surface, it may have any shape that is convenient for actuation by an operator. For example, control button 14 may have an angled, concave, rounded, or dimpled surface, or the control button 14 may take the form of a joystick.

Figure 2:
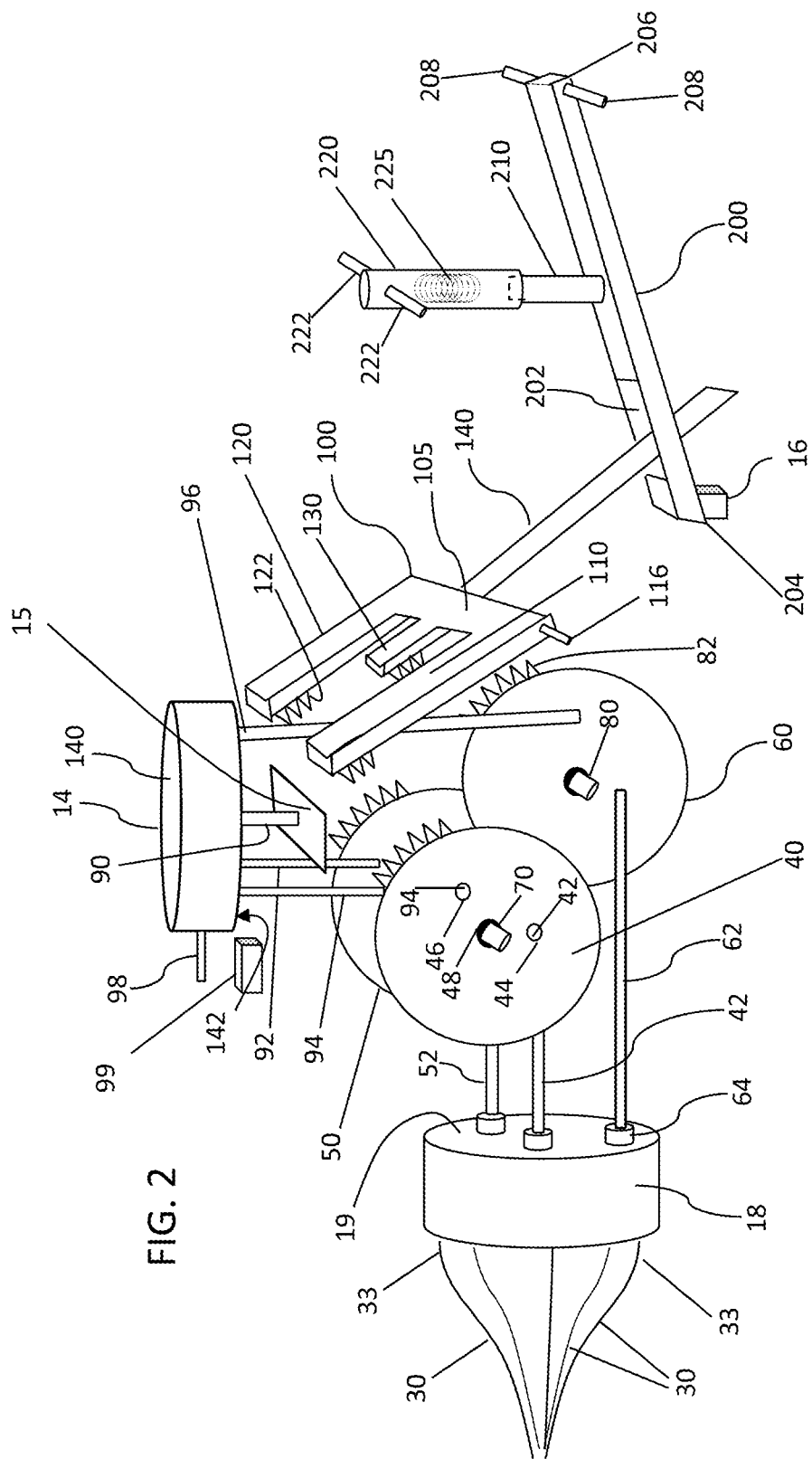
FIG. 2 shows an exemplary embodiment of the operative mechanism for steering and locking the steerable guidewire in a neutral configuration.

The plurality of wires 30 may attach to the wire attachment disc 18 at the proximal ends 33 of the wires 30 (FIG. 2). The wires 30 may attach anywhere on the wire attachment disc 18 suitable for creating differing tension in the wires 30 as the orientation of the face 17 of the wire attachment disc 18 changes. For example, the wires 30 may attach at peripheral locations on the face 17 of the wire attachment disc 18, or the wires 30 may alternatively attach to the sides of the disc 18. FIG. 1B shows five miniature wires 30 attached to the face 17 of the wire attachment disc 18. However, the invention is not limited to this specific number of wires. Generally at least three wires are needed. Five to six wires are preferred.

FIG. 2 illustrates one embodiment of the working mechanism for controlling the orientation of the wire attachment disc 18 and the distal end 31 of the plurality of wires 30. The control button 14 is operatively connected to a first wheel 40, a second wheel 50, and a third wheel 60. In FIG. 2, the operative connections are in the form of a first force-transmittal rod 94, a second force-transmittal rod 92, and a third force transmittal rod 96, which connect, respectively, the first, second, and third wheels 40, 50, 60 to the control button 14. The control button 14 has a top surface 140 and a bottom surface 142. The top surface 140 may lie above the first opening 20 for ease of access/actuation by an operator. The bottom surface 142 may connect to an optional pivot rod 90. Pivot rod 90 and the control button 14 may be integral or the pivot rod 90 may fit into a recessed area on the bottom of the control button 14 or the bottom of the control button 14 may have bosses 144 (FIG. 4) situated thereon, into which fit the pivot rod 90, and first, second, and third force-transmittal rods 94, 92, and 96. Each of the first, second, and third force-transmittal rods 94, 92, and 96 has a first end and a second end, the first ends being connected to the wheels 40, 50, and 60 and second ends being connected to the control button 14.

In the exemplary embodiment of FIG. 2, the pivot rod 90 contacts an optional pivot plate 15 that is situated below the control button 14 and above the first, second, and third wheels 40, 50, and 60. Thus, the pivot rod 90 may space the control button 14 from pivot plate 15. Alternatively, the pivot rod 90 may be a spring attached to both the bottom surface of the control button 14 and the top surface of the pivot plate 15. The pivot plate 90 may be mounted to the interior of the housing 12 and may have any shape suitable for internal mounting that does not interfere with the movement of the force-transmittal rods 92, 94, and 96. A stop rod 98 may be optionally attached to the front of the control button 14. The stop rod 98 limits the maximum tilt angle of the control button 14 by contacting an interior surface element 99 of the housing 12 at the designated maximum tilt angle.

The first, second, and third wheels 40, 50, and 60 are rotatably mounted to the interior of the housing. In FIG. 2, wheels 40 and 50 are mounted on an axle 70 that passes through an aperture in each wheel like aperture 48 in the first wheel 40. The third wheel 60 may be rotatably mounted on a separate axle 80. The axles 70 and 80 may be attached to the side inner walls of the housing. For example, the axles 70 and 80 may fit into bosses 72 on the side inner walls 270 of the housing (FIG. 4). The connections between each of the first, second, and third force-transmittal rods 94, 92, and 96 and the first, second, and third wheels 40, 50, and 60 allow the wheels to rotate about their respective axles. For example, the first, second, and third force-transmittal rods 94, 92, and 96 may connect to the first, second, and third wheels 40, 50, 60 through apertures in the first, second, and third wheels 40, 50, 60 such as the aperture 46 in the first wheel 40. Although the first and second wheels 40 and 50 are described as mounted to the same axle, they may be mounted individually on different axles and the axles on which they are mounted (including for the third wheel 60) may be mounted on any convenient location inside the housing and not necessarily limited to the side inner walls. The entire handle and its operative mechanism may be made of plastic. Preferably, the axles are made of metal and the wheels and rods molded from plastic.

The wire attachment disc 18 has a face 17, a back 19, a vertical axis 180 (FIG. 4), and a horizontal axis 182. The first, second, and third wheels 40, 50, and 60 are operatively connected to the wire attachment disc 18. In FIG. 2, the operative connection is in the form of a first force-receiving rod 42, a second force-receiving rod 52, and a third force-receiving rod 62, which connect, respectively, the first, second, and third wheels 40, 50, 60 to the wire attachment disc 18. In FIG. 2, the first, second, and third force-receiving rods 42, 52, and 62 connect to wire attachment disc 18 by fitting into bosses 64 on the back 19 of the wire attachment disc 18. Each of the first, second, and third force-receiving rods 42, 52, and 62 has a first end and a second end, the first ends being connected to the wheels 40, 50, and 60 and the second ends being connected to the wire attachment disc 18. The connections between each of the first, second, and third force-receiving rods 42, 52, and 62 and the first, second, and third wheels 40, 50, and 60 allow the wheels to rotate about their respective axles. For example, the first, second, and third force-receiving rods 42, 52, and 62 may connect to the first, second, and third wheels 40, 50, 60 through apertures in the wheels such as aperture 44. Although the force-transmittal and force-receiving rods 94, 92, 96, 42, 52, and 62 in FIG. 2 are described as inserting into an aperture in the first, second, and third wheels 40, 50, 60, this arrangement may be reversed. For example, each wheel may have a nub or projecting element that fits into an aperture at the end of the rods. Depending on the sizes of the rods used, the area of attachment on the rods may need to be enlarged somewhat relative to the rest of the rod in order to accommodate the needed aperture in the end of the rods.

Also shown in FIG. 2 is one embodiment of a locking mechanism for a steerable guidewire assembly. The locking feature allows an operator to maintain the tip of the guidewire at a desired angle during an interventional procedure. The locking feature in FIG. 2 includes a set of locking arms 100. The set of locking arms may have a first arm 110, a second arm 120, and a third arm 130, each of which is connected to a base 105. The set of locking arms 100 is adapted to engage the first, second, and third wheels 40, 50, 60 and brake the rotational movement of the wheels. In FIG. 2, the locking arms 110, 120, and 130 have teeth 122 that may engage opposing teeth 82 on the first, second, and third wheels 40, 50, 60. The set of locking arms 100 may engage the wheels 40, 50, and 60 by rotating forward and downward about an axle 116 that may be attached to the side inner walls of the housing 12.

The forward/downward rotation of the set of locking arms 100 may be controlled by lifting on a first lever arm 140 that is also attached to the base 105. A second lever arm 200 may be lifted by the application of upward force on the locking button 16 that may be located on a first end 204 of the second lever arm 200. Upward motion of the second lever arm 200 contacts the first lever arm 140 thereby raising it and simultaneously lowering the set of locking arms 100 into engagement with the wheels 40, 50, and 60 as the locking arms 110, 120, 130 rotate forward and downward about the axle 116. In FIG. 2, the first lever arm 140 extends through an opening 202 in the second lever arm 200.

In the embodiment of FIG. 2, the second lever arm 200 is rotatably mounted to the side inner walls of the housing 12 by an axle 208 located at a second end 206 of the second lever arm 200. A piston 210 fits into a cylinder 220 loaded with a spring 225 that is compressed by the piston 210 as the second lever arm 200 is lifted upward. The cylinder 220 may be mounted by rod 222 to the side inner walls 270 of the housing 12. The spring 225 in the cylinder 220 provides a downward force to release the locking arms 100 once the locking button 16 is no longer depressed. This allows the operator to use the handle at any angle without needing to rely solely on gravitational force to maintain the set locking arms 100 out of engagement with the wheels 40, 50, and 60.

FIG. 2 illustrates just one possible means for locking the wheels 40, 50, and 60 in position. The teeth 82 and 122, for example, may have any shape that allows interlocking of the opposing teeth. Also, the positioning and the number of teeth are not limited by the embodiments shown in FIGS. 2 and 3. It will be appreciated by those skilled in the art that the number and positioning of the teeth can be adjusted so as to provide for optimal functional interlocking of the opposing teeth on the wheels and locking arms. As an alternative to the use of interlocking teeth, the first, second, and third wheels 40, 50, and 60 may be held in place by frictional contact between the wheels and the set locking arms 100.

Figure 3:
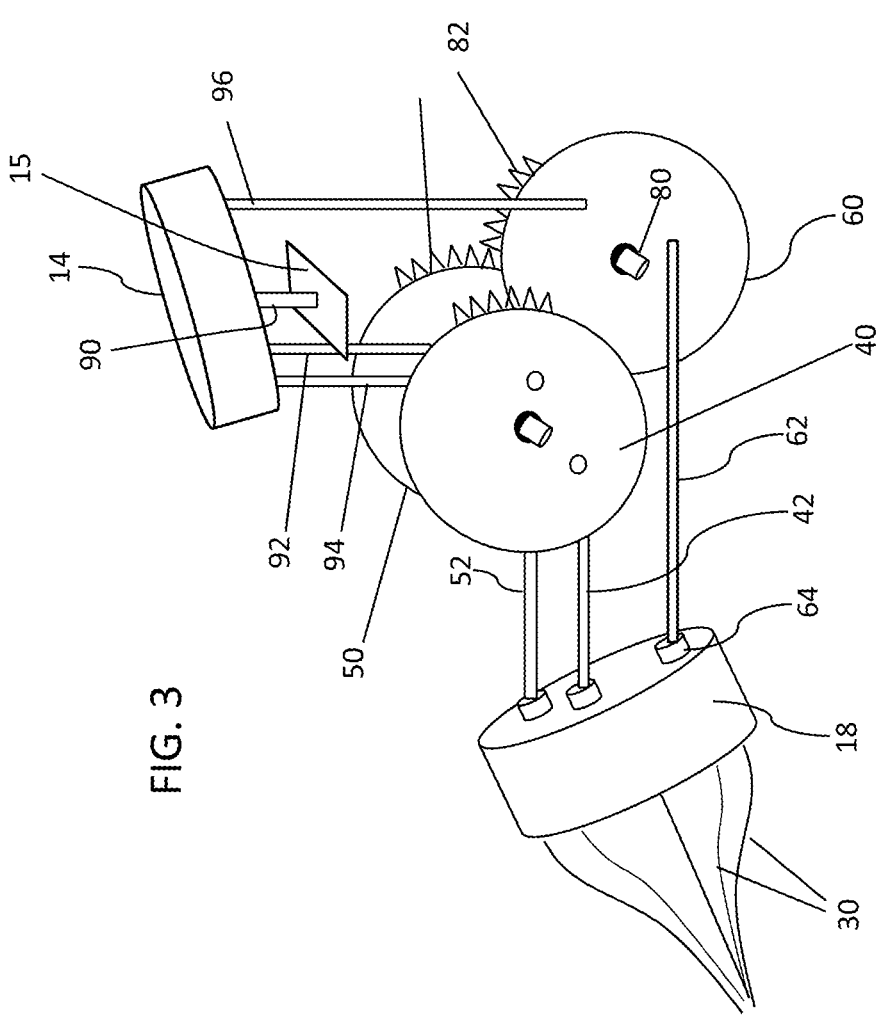
FIG. 3 illustrates a representative configuration viewed from the side where the face of the wire attachment disc is tipped downward away from a vertical position.

In FIG. 2, the operating mechanism for the steerable guidewire 2 is in a neutral configuration such that the distal end 31 of the plurality of wires 30 adopts a substantially straight orientation. Movement of the control button 14 changes the orientation of the wire attachment disc 18 and thereby deflects the distal end 31 of the guidewire in the desired direction. As shown in FIG. 3, rocking the control button 14 forward pushes down on the first and second force-transmittal rods 94 and 92 to rotate the first and second wheels 40 and 50 in a clockwise direction when viewed from the left side of the handle 10. Simultaneously, the third force-transmittal rod 96 is pulled up to rotate the third wheel 60 in a counterclockwise direction as seen from the left side. In the configuration in FIG. 3, the first and second force-receiving rods 42 and 52 are moved forward by the rotation of the first and second wheels 40 and 50 at the same time as the third force-receiving rod 62 is retracted backward by the rotation of the third wheel 60. The combined forward motion of force-receiving rods 42 and 52 and rearward motion of force-receiving rod 62 tips the face 17 of the wire attachment disc 18 downward away from a vertical orientation. It is also contemplated within the scope of the invention to have more than three wheels to control the orientation of the wire attachment disc, such as, for example having a fourth wheel and corresponding rods.

As will be appreciated from the foregoing description, a backward rocking movement of the control button 14 moves the wheels 40, 50, and 60 and rods 94, 92, 96, 42, 52, and 62 in the directions opposite to that in FIG. 3, thereby resulting in an upward orientation of the face 17 of the wire attachment disc 18. Although FIGS. 2 and 3 show the first and second wheels 40 and 50 in a forward position relative to the third wheel 60, these positions can also be reversed. Likewise, the relative vertical positions of the first, second, and third wheels 40, 50, and 60 can be changed or both the vertical and horizontal positions of the wheels can be interchanged. Although different positioning of the three wheels in FIGS. 2 and 3 is possible and may result in the control button 14 producing an opposite orientation of the face of the wire attachment disc relative to that in FIG. 3, the principle of operation of the rods and wheels nonetheless remains the same.

FIG. 4 illustrates a configuration where the control button 14 has been rocked to the right side of the handle 10. In this configuration, the second force-transmittal rod 92 is pushed downward while the first force-transmittal rod 94 is pulled upward. These movements of the rods 92 and 94 rotate the first and second wheels 40 and 50 in opposite directions, the first wheel 40 is rotated in a counterclockwise direction and the second wheel 50 is rotated in a clockwise direction, each as viewed from the left side. The opposing rotations of the first and second wheels 40 and 50 twist the wire attachment disc 18 about its vertical axis 180 by the relative movement of the first and second force-receiving rods, which are not shown in FIG. 4. Rocking the control button 14 to the left produces the opposite effect with the disc 18 twisting to the right due to the forward movement of the first force-receiving rod and the rearward movement of the second force-receiving rod. When the control button 14 is rocked side-to-side, the third force-transmittal rod 96 and third wheel 60 remain in a neutral configuration.

The rods 42, 52, 62, 92, 94, and 96 are connected to wheels 40, 50, and 60 at a radial distance from the center of each wheel so as to allow sufficient movement of the wire attachment disc 18 to deflect the tip of the guidewire. The further out the connection point from the center of the wheels 40, 50, and 60, the less movement of the wire attachment disc 18 is produced for a given amount of movement of the control button 14. Finer control, however, may be obtained by situating the connection point further from the center of the wheels 40, 50, and 60.

For ease of illustration, FIGS. 3 and 4 show only two possible configurations for the control button 14 and wire attachment disc 18. However, the forward-backward and side-to-side movement of the control button 14 are not exclusive of each other. The control button 14 can be rocked throughout a 360° range of motion to provide for orientation of the wire attachment disc 18 in any direction and correspondingly deflection of the tip of the guidewire in any desired direction. In other words, the control button 14 can be rocked to positions that combine the forward-backward and side-to-side movements to allow configurations that are intermediate between those in FIGS. 3 and 4. Preferably, the tip of the guidewire may be deflected at any angle up to about 90° and the direction of the deflection may be to any position throughout the 360° about the axis of the guidewire.

FIG. 5 illustrates the effect on the distal end 31 of the plurality of wires 30 by tipping the wire attachment disc 18 away from a vertical orientation or of twisting the wire attachment disc 18 about its vertical axis. The individual wires of the plurality of wires 30 are operatively joined as described herein below to allow deflection of the tip. The tipping/twisting movement puts greater tension on wires 30c and 30d such that these wires are pulled back relative to wires 30a and 30b, for which the tension is reduced or remains unchanged. The distal end 31 of the plurality of wires 30 is deflected in the direction of the wires subject to the greater tension. Returning the wire attachment disc 18 to a neutral configuration straightens the distal end 31 of the plurality of wires 30.

The sheath 35 may have small interior channels 39 (FIG. 6A) that extend substantially the length of the sheath and through which pass the individual wires 30 of the plurality of wires. The channels may have a circular cross-sectional shape as in FIG. 6A or they may be formed as a hollow protrusion from the interior of the sheath with a semi-circular cross-section. The channels 39 help prevent the wires 30 from tangling inside the sheath 35 by keeping the wires 30 in the same register from the wire attachment disc 18 to the distal end of the guidewire. The channels 39 may be continuous or discontinuous.

To achieve the deflection of the tip as in FIG. 5, the distal ends of the individual wires are operatively joined to each other such that differing tensions in the individual wires allow the tip to deflect. The operative connection may be formed by connection of each wire to an intermediate structure that allows communication of the tensions in the individual wires. For example, at the distal end of the sheath 35, the wires may be affixed to a spring 300 or other structure so as to allow deflection of the distal end of the guidewire. The spring 300 may be an extension of the sheath 35, or a separate spring 300 may traverse the length of the interior of the sheath 35. Thus, the sheath may include a portion formed of a flexible solid-walled tubing and a portion that is a laterally flexible spring or coil. The spacings between the windings of the spring at the distal end allows for lateral flexibility so the tip can deflect. Alternatively, the wires 30 may be bonded to the interior of the distal end of the sheath 35 so that tension on wires 30d and 30c tips the sheath itself in the direction of tension.

To provide for lateral flexibility, certain embodiments may include a spring 300 (FIG. 6B) that may be surrounded by a sheath 35 and through which pass the wires 30, either with or without the channels 39. Alternatively, the sheath 35 may be omitted. In an alternative embodiment, the wires may traverse through passages 320 in a series of articulated miniature spheres 310 (FIG. 6C), or other similar structure that is enclosed within a sheath 35. The distal ends 31 of the wires 30 may be attached to a sphere at the distal end such that tension on a wire(s) deflects the tip in the direction of the tension. In this latter arrangement, the sheath may also be omitted. Certain embodiments may have a combination of springs and spheres. In certain embodiments, the distal end of the sheath 35 may comprise a spring and the wires 30 may extend beyond the end of the spring portion of the sheath and terminate in an operative connection by attachment to a sphere 310 or a hemispherical structure. In other embodiments, the distal end of the sheath 35 need not comprise a spring, where the wires 30 extend beyond the distal end of the sheath and are operatively connected to the sphere or hemisphere. Or the wires 30 may attach to the end of the spring, with a hemispherical structure attached to the end of the spring. Preferably the guidewire tip has a hemispherical or rounded surface to be atraumatic to surrounding tissue.

The individual wires that make up the plurality of wires are preferably made of a material that has both flexibility and high tensile strength. Examples of suitable materials for the wires are stainless steel, tungsten, and cobalt-chromium. The wires have a sufficient tensile strength that allows the tension in a wire to deflect the tip of the guidewire without breaking the individual wire. Yet, the wires also have flexibility to navigate tortuous pathways in the vasculature. The wires may also be Teflon coated. The individual wires may be composed of still smaller individual wirelets that are either braided or stranded.

The individual wires of the plurality of wires may each have a diameter in the range of about 0.0025 to about 0.005 inches and may be attached to the wire attachment disc using any suitable method such as with the use of set screws. The individual wirelets may each have a diameter in the range of about 0.0001 to about 0.002 inches.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

What is claimed is:

1. A steerable intraluminal medical device comprising:
   a handle, the handle comprising
      a housing, the housing having an interior and an exterior;
      a first wheel, the first wheel being rotatably mounted on the interior of the housing;
      a first force-transmittal rod, the first force-transmittal first rod having a first end and a second end, the first end being connected to the first wheel;
      a first force-receiving rod, the first force-receiving rod having a first end and a second end, the first end being connected to the first wheel;
      a control button, the control button having a top surface, the top surface being actuatable by an operator, the control button being connected to the second end of the first force-transmittal rod;
      a wire attachment disc, the wire attachment disc being connected to the second end of the first force-receiving rod; and
   a plurality of wires, the plurality of wires having proximal ends and distal ends, the proximal ends being attached to the handle at the wire attachment disc, the plurality of wires being operatively joined at their distal ends; and
   a sheath, the sheath surrounding a portion of the plurality of wires.

2. The intraluminal medical device of claim 1 further comprising
   a second wheel, the second wheel being rotatably mounted on the interior of the housing;
   a second force-transmittal rod, the second force-transmittal first rod having a first end and a second end, the first end being connected to the second wheel and the second end being connected to the control button; and
   a second force-receiving rod, the second force-receiving rod having a first end and a second end, the first end being connected to the second wheel and the second end being connected to the wire attachment disc.

3. The intraluminal medical device of claim 2 further comprising
   a third wheel, the third wheel being rotatably mounted on the interior of the housing;
   a third force-transmittal rod, the third force-transmittal first rod having a first end and a second end, the first end being connected to the third wheel and the second end being connected to the control button; and
   a third force-receiving rod, the third force-receiving rod having a first end and a second end, the first end being connected to the third wheel and the second end being connected to the wire attachment disc.

4. The intraluminal medical device of claim 3, wherein the handle further comprises a set of locking arms, the set of locking arms being mounted to the interior of the housing and comprising a first arm, a second arm, and a third arm, the first, second, and third arms being adapted to brake, respectively, the first, second, and third wheels.

5. The intraluminal medical device of claim 4 wherein the first, second, and third wheels and the first, second, and third arms each independently comprises a set of teeth, each set of teeth being positioned such that the teeth on the first, second, and third arms are capable of engaging, respectively, the teeth on the first, second, and third wheels.

6. The intraluminal medical device of claim 5 wherein the set of locking arms is rotatably mounted to the interior of the housing.

7. The intraluminal medical device of claim 6 further comprising:
   a first lever arm, the first lever arm having a first end and a second end, the first end being attached to the set of locking arms;
   a second lever arm, the second lever arm having a first end and a second end, the second end being rotatably mounted on the interior of the housing; and
   a locking button, the locking button being connected to the first end of the second lever arm and actuatable by an operator;
   wherein actuation of the locking button raises the first end of the second lever arm into engagement with the second end of the first lever arm, thereby rotating the set of locking arms downward.

8. The intraluminal medical device of claim 7 further comprising:
   a cylinder, the cylinder being attached to the interior of the housing;
   a spring, the spring being located inside the cylinder; and
   a piston, the piston being attached to the second lever arm, wherein the cylinder and the piston are positioned such that the cylinder receives the piston and the piston compresses the spring when the second lever arm is raised by actuation of the locking button.

9. The intraluminal medical device of claim 1 wherein the sheath further comprises a plurality of continuous channels, each wire of the plurality of wires occupying an independent channel of the plurality of continuous channels.

10. The intraluminal medical device of claim 1 wherein the distal ends of the plurality of wires are fixed to the distal end of the sheath.

11. The intraluminal medical device of any one of claims 1-9 wherein the sheath has a distal end and a portion of each wire of the plurality of wires extends beyond the distal end of the sheath and the distal ends of the wires are operatively joined at the portions that extend beyond the distal end of the sheath.

12. The intraluminal medical device of claim 7 wherein the housing further comprises a top, a bottom, and a front, the control button being actuatable from the top, the wire attachment disc being located on the front, and the locking button being actuatable from the bottom.

13. The intraluminal medical device of claim 1 wherein the sheath comprises a spring.

14. The intraluminal medical device of claim 1 wherein the plurality of wires comprises five or six wires.

15. The intraluminal medical device of claim 1 further comprising:
   a pivot plate, the pivot plate being mounted to the interior of the housing; and
   a pivot rod, the pivot spacing the control button from the pivot plate.

16. A steerable intraluminal medical device comprising:
   a handle, the handle comprising
      a housing, the housing having an interior and an exterior;
      a first wheel, a second wheel, and a third wheel, the first, second, and third wheels being rotatably mounted on the interior of the housing;
      a control button, the control button being operatively connected to the first, second and third wheels such that movement of the control button independently controls rotation of the first, second, and third wheels; and
      a wire attachment disc, the wire attachment disc being operatively connected to the first second and third wheels such that independent rotation of the first, second, and third wheels changes the orientation of the wire attachment disc;
   a plurality of wires, the plurality of wires having proximal ends and distal ends, the proximal ends being attached to the handle at the wire attachment disc, the plurality of wires being operatively joined at their distal ends; and
   a sheath, the sheath surrounding a portion of the plurality of wires.

17. The intraluminal medical device of claim 16 wherein:
a forward movement of the control button rotates the first and second wheels in a first direction and the third wheel in a second direction opposite the first direction; and a side-to-side movement of the control button rotates the first and second wheels in opposite directions.

18. The intraluminal medical device of claim 17 wherein:
the wire attachment disc has a vertical axis and a horizontal axis, wherein rotation of the first and second wheels in the first direction tilts the wire attachment disc away from a vertical orientation and rotation of the first and second wheels in opposite directions twists the wire attachment disc around the vertical axis.

19. The intraluminal medical device of claim 16 further comprising
a set of locking arms, the set of locking arms being mounted to the interior of the housing and comprising a first arm, a second arm, and a third arm, the first, second, and third arms being adapted to brake, respectively, the first, second, and third wheels.

20. The intraluminal medical device of claim 19 further comprising:
a locking button, the locking button having a surface actuatable by an operator, wherein the locking button is operatively connected to the set of locking arms.

\* \* \* \* \*